United States Patent
Clark

(10) Patent No.: US 6,534,475 B1
(45) Date of Patent: Mar. 18, 2003

(54) USE OF TIMP-3 INDUCERS OF TIMP-3 EXPRESSION, AND TIMP-3 MIMETICS TO TREAT OCULAR NEOVASCULARIZATION

(75) Inventor: Abbot F. Clark, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 21 days.

(21) Appl. No.: 09/697,568

(22) Filed: Oct. 26, 2000

Related U.S. Application Data

(60) Provisional application No. 60/166,127, filed on Nov. 18, 1999.

(51) Int. Cl.$^7$ .......................... A61K 38/00; A61K 38/16
(52) U.S. Cl. ............................. 514/2; 514/8; 514/912; 514/913
(58) Field of Search .............................. 514/912, 913, 514/2, 8

(56) References Cited

PUBLICATIONS

Wojtowicz–Praga, et al., "Matrix metalloproteinase inhibitors," *Invest New Drugs*, vol. 15(1):61–75, 1997.

Della, et al., "Localization of TIMP–3 mRNA Expression to the Retinal Pigment Epithelium," *Invest. Ophthal. & Visual Science*, vol. 37(9):1921–22, Aug., 1996.

Ruiz, et al., "TIMP–3 is Expressed in the Human Retinal Pigment Epithelium," *Biochemical and Biophysical Res. Comm.*, vol. 226(2):467–474, 1996.

Vranka, et al., "Discrete Expression and Distribution Pattern of TIMP–3 in the Human Retina and Choroid," *Current Eye Research*, p. 102–109, 1996.

Fariss, et al., "Tissue Inhibitor of Metalloproteinases–3 Is a Component of Bruch's Membrane of the Eye," *American Journal of Pathology*, vol. 150(1):323–326, Jan., 1997.

Anand–Apte, et al., "Inhibition of Angiogenesis by Tissue Inhibitor of Metalloproteinase–3," *Invest. Ophthal. & Visual Science*, vol. 38(5):817–821, Apr., 1997.

Weber, et al., "Mutations in the tissue inhibitor of metalloproteinases–3 (TIMP3) in patients with Sorsby's fundus dystrophy," *Nature Genetics*, vol. 8:352–356, 1994.

Felbor, et al., "Evaluation of the Gene Encoding the Tissue Inhibitor of Metalloproteinases–3 in Various Maculopathies," *Invest. Ophthal. & Visual Science*, vol. 38(6):1054–1059, May, 1997.

*Primary Examiner*—Zohreh Fay
(74) *Attorney, Agent, or Firm*—Sally Yeager

(57) ABSTRACT

Methods and compositions for treating ocular neovascularization with TIMP-3, TIMP-3 inducers, and TIMP-3 mimetics are disclosed.

1 Claim, No Drawings

USE OF TIMP-3 INDUCERS OF TIMP-3 EXPRESSION, AND TIMP-3 MIMETICS TO TREAT OCULAR NEOVASCULARIZATION

This application claims priority from U.S. Provisional Application Ser. No. 60/166,127 filed Nov. 18, 1999. The present invention is directed to the use of tissue inhibitors of metalloproteinases-3 (TIMP-3), inducers of TIMP-3, and TIMP-3 mimetics to prevent and/or treat ocular neovascularization.

BACKGROUND OF THE INVENTION

There has been a great deal of interest in matrix metalloproteinases (MMPs) and tissue inhibitors of metalloproteinases (TIMPs) over the past several years particularly related to the role of these molecules in cancer biology. MMPs are responsible for the invasion of tumors into normal tissue, tumor angiogenesis, and metastasis. There is a large body of research directed at finding MMP antagonists for the treatment of cancer (see e.g. Wojtowicz-Praga, et al., "Matrix metalloproteinase inhibitors," *Invest New Drugs*, Vol. 15(1):61–75, 1997).

TIMP-3 is a member of a family of natural proteins which inhibit the activities of MMPs. There are at least 15 distinct MMPs with differing, but often overlapping, specificities which are responsible for degrading extracellular matrix molecules and breaking down (turning-over) the extracellular matrix of tissues and cells. TIMPs help to regulate the activity of MMPs and thereby control the extracellular matrix environment.

There are a variety of diseases and conditions that cause neovascularization in the eye which results in the loss of vision. One rate limiting step in the neovascular process is the breakdown of the basement membrane enclosing vascular endothelial cells which allows the vascular endothelial cells to migrate towards the angiogenic signal, proliferate, and form new capillaries. MMPs are responsible for this initial step in neovascularization, and a therapy directed towards inhibiting these MMPs would be angiostatic. TIMP-3 is a "natural" angiostatic agent which is made by retinal pigment epithelial cells (Della, et al., "Localization of TIMP-3 mRNA Expression to the Retinal Pigment Epithelium," *Invest. Ophthal. & Visual Science*, Vol. 37(9): 1921–22, August, 1996; Ruiz, et al., "TIMP-3 is Expressed in the Human Retinal Pigment Epithelium," *Biochemical and Biophysical Res. Comm.*, Vol. 226(2):467–474, 1996) and resides in Bruch's membrane between the choroid and retinal pigment epithelium (Vranka, et al., "Discrete Expression and Distribution Pattern of TIMP-3 in the Human Retina and Choroid," *Current Eye Research*, pg. 102–109, 1996; Fariss, et al., "Tissue Inhibitor of Metalloproteinases-3 Is a Component of Bruch's Membrane of the Eye," *American Journal of Pathology*, Vol. 150(1): 323–326, January, 1997) effectively providing an angiostatic barrier to the choroid. TIMP-3 has been shown to have angiostatic activity in vitro (Anand-Apte, et al., "Inhibition of Angiogenesis by Tissue Inhibitor of Metalloproteinase-3," *Invest. Ophthal. & Visual Science*, Vol. 38(5):817–821, April, 1997). Mutations in TIMP-3 are responsible for an inherited condition, Sorsby's fundus dystrophy (Weber, et al., "Mutations in the tissue inhibitor of metalloproteinases-3 (TIMP3) in patients with Sorsby's fundus dystrophy," *Nature Genetics*, Vol. 8:352–356, 1994; Felbor, et al., "Evaluation of the Gene Encoding the Tissue Inhibitor of Metalloproteinases-3 in Various Maculopathies," *Invest. Ophthal. & Visual Science*, Vol. 38(6):1054–1059, May, 1997), which is characterized by subretinal neovascularization and hemorrhage and is clinically similar to the wet form of age-related macular degeneration (ARMD).

Diabetic retinopathy is currently treated with panretinal photocoagulation which destroys healthy retinal tissue to inhibit further neovascularization. Sub-foveal and juxtafoveal neovascular membranes in ARMD are treated with laser photocoagulation which causes an immediate vision loss in attempt to prevent further growth of the neovascular membrane. There are currently no effective therapies which inhibit ocular neovascularization without also causing the destruction of healthy tissue. The proposed invention would provide a method of inhibiting the neovascular disease process at an initial step in the neovascularization pathway.

SUMMARY OF THE INVENTION

The present invention is directed do compositions and methods for treating conditions associated with ocular neovascularization, specifically, corneal neovascularization, rubeosis iridis, neovascular glaucoma, age-related macular degeneration, diabetic retinopathy, ischemic retinopathy, and retinopathy of prematurity.

DETAILED DESCRIPTION OF THE PREFERRED EMBODIMENTS

The present invention is directed to the treatment of ocular neovascularization using a unique class of agents which include TIMP-3, agents which stimulate TIMP-3 expression, and TIMP-3 mimetics. These agents can be delivered by transplantation of cells expressing TIMP-3, transfection with vectors which carry and express TIMP-3 DNA, agents that induce the expression of endogenous TIMP-3, or by oral, topical, periocular or intraocular administration of TIMP-3 mimetics.

The present invention will inhibit a rate limiting step in ocular neovascularization and inhibit ocular neovascularization without the destruction of healthy ocular tissue (which occurs with current therapies). The proposed therapy should also inhibit the neovascular process independent of the inciting cause (i.e. independent of the angiogenic signal).

Agents which are useful according to the present invention include, but are not limited to TIMP-3, agents that induce TIMP-3 expression, TIMP-3 expression vectors, and TIMP-3 mimetics. Further compounds can be elucidated through the use of known assays, such as, in vitro MMP activity assays, cell-based TIMP-3 expression assays, and a variety of angiogenesis assays (chick embryo CAM, corneal pocket model of neovascularization, retinopathy of prematurity models, subretinal neovascularization models, the developing mouse retinal model of neovascularization, etc. These models are known to people skilled in the art).

The compounds or agents, particularly TIMP-3 mimetics and TIMP-3 inducers, can be incorporated into various types of ophthalmic formulations for delivery to the eye. These agents may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solution may also contain a thickener such as hydroxymethylcellulose, hydroxyethylcellulose, hydroxypropylmethylcellulose, methylcellulose, polyvinylpyrrolidone, or the like, to improve the retention of the formulation in the conjunctival sac. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

The compounds are preferably formulated as topical ophthalmic suspensions or solutions, with a pH of about 4 to 10. The compounds will normally be contained in these formulations in an amount 0.001% to 10% by weight, but preferably in an amount of 0.01% to 1% by weight. Thus, for topical presentation 1 to 3 drops of these formulations would be delivered to the surface of the eye 1 to 4 times per day according to the routine discretion of a skilled clinician.

I claim:

1. A method for treating ocular neovascularization selected from the group consisting of corneal neovascularization, rubeosis iridis, neovascular glaucoma, age- related macular degeneration, diabetic retinopathy, ischemic retinopathy, and retinopathy of prematurity which comprises administering a pharmaceutically effective amount of a composition comprising a compound selected from the group consisting of TIMP-3, TIMP-3 inducers, and TIMP 3 mimetics.

* * * * *